United States Patent [19]

Bernstein et al.

[11] 3,968,249
[45] July 6, 1976

[54] METHOD OF TREATING MALIGNANT NEOPLASTIC DISEASE

[75] Inventors: Jack Bernstein, New Brunswick; Barbara Stearns, Highland Park, both of N.J.

[73] Assignee: E. R. Squibb & Sons, Inc., Princeton, N.J.

[22] Filed: May 15, 1968

[21] Appl. No.: 729,450

Related U.S. Application Data

[63] Continuation-in-part of Ser. No. 253,031, Jan. 22, 1963, abandoned, which is a continuation-in-part of Ser. No. 862,452, Dec. 29, 1959, abandoned.

[52] U.S. Cl. .............................................. 424/322
[51] Int. Cl.$^2$......................................... A61K 31/17
[58] Field of Search .................................. 424/322

[56] References Cited
OTHER PUBLICATIONS

Tarnowski, Cancer Research, vol. 18, No. 8, part 2, Sept., 1958, pp. 1–5 and 45.

Cecil, A Textbook of Medicine, 1958, Ninth Edition, W. B. Saunders Co., Philadelphia, p. 1215.

Dorland, Medical Dictionary, 18th Edition, 1938, W. B. Saunders Co., pp. 266–267.

*Primary Examiner*—Jerome D. Goldberg
*Attorney, Agent, or Firm*—Lawrence S. Levinson; Merle J. Smith

[57] ABSTRACT

This invention relates to pharmaceutical preparations and the method of utilizing them in the treatment of malignant neoplastic diseases. The administration of hydroxyurea or 1-ethyl-1-hydroxyurea has been found to be effective for the amelioration of the symptoms of various forms of leukemia, carcinoma or sarcoma in various organs of the body.

10 Claims, No Drawings

METHOD OF TREATING MALIGNANT NEOPLASTIC DISEASE

SUMMARY OF THE INVENTION

This invention relates to pharmaceutical preparations which are effective as a method of treating and ameliorating the symptoms of malignant neoplastic diseases, such as various forms of leukemia, carcinoma and sarcoma in various organs of the body.

A large number of chemical compounds have been studied in an effort to find an effective means for the suppression and/or amelioration of malignancies like leukemia, carcinoma and sarcoma and of the organic changes associated therewith. Unfortunately, no compound thus far tested has proved effective for the total remission of such diseases. However, while the total remission remains the ultimate objective, the desirability of providing suitable means for relieving the symptoms is beyond question. Hence, the provision of compounds and of therapeutic compositions which can be employed even for the partial or temporary remission of leukemia, carcinoma or sarcoma symptoms constitutes a major demand in modern medicine. It has been found in accordance with the present invention that the administration of hydroxyurea or 1-ethyl-1-hydroxyurea elicits a beneficial response in sufferers with such symptoms.

It has been found that objective remission of the disease can be obtained in many instances by the oral or parenteral administration, e.g., intravenous infusion or intraperitoneal injection, of hydroxyurea or 1-ethyl-1-hydroxyurea. The dosage schedule may be varied within rather broad limits as the case requires, about 20 to 80 mg./kg., e.g., about 50 mg. to 4 grams daily, in single doses or 3 to 4 divided doses. Preferably a dosage of about 20 to 60 mg. per kg. per day, or a total of about 1 gm. to 4 gm. per day orally is used. About 50 mg./kg., at least initially, is recommended to obtain a response in the malignancy without undue manifestation of toxic symptoms. Maintenance doses may be maintained at the same level or reduced to a lower level as required. Intermittent administration of about 80 mg./kg. orally as a single dose every third day may also be used. Concomitant or intermittent irradiation or hormone therapy may also be utilized in conjunction with the administration of hydroxyurea or 1-ethyl-1-hydroxyurea.

Objective responses or tumor regressions may be obtained in various forms of leukemia, carcinoma, sarcoma or related neoplasms including, for example, leukemia such as chronic myelocytic leukemia, chronic lymphocytic leukemia, acute myeloblastic leukemia, acute myelogenous leukemia, acute lymphoblastic leukemia, acute stem cell leukemia or Naegeli type leukemia; lymphomas, lymphosarcomas and related neoplasms such as multiple myeloma, Hodgkin's granuloma, Hodgkin's sarcoma, lymphoma, malignant lymphoma, lymphosarcoma, reticulum cell sarcoma; carcinomas such as squamous cell or epidermoid carcinoma, adenocarcinoma, anaplastic carcinoma, undifferentiated carcinoma, transitional cell carcinoma, renal cell carcinoma or hypernephroma, melanoma, hepatoma, granulosa cell carcinoma or scirrhous carcinoma, sarcomas such as chondrosarcoma, fibrosarcoma, leiomyosarcoma, liposarcoma or synoviosarcoma; mixed cell types such as gliobastoma multiformi, neuroblastoma or the like. Such malignant neoplastic diseases occur in various body parts or organs such as the brain, small intestine, breast, ovary, testes, stomach, lung, pancreas, rectum, head, neck, urinary bladder, cervix, prostate, thyroid, uterus, kidney, esphagus, vulva, liver, skin, bone or muscle. Significant responses are obtained in particular in squamous cell carcinoma especially in the lung, head and neck, carcinoma of the urinary bladder, particularly transitional cell carcinoma, adenocarcinoma, especially in the breast, endometrium, ovary and stomach, granulosa cell carcinoma, especially in the ovary, anaplastic carcinoma of the breast, transitional cell carcinoma, chronic myelocytic leukemia, hypernephroma, melanoma, miscellaneous tumors in the ovaries and testes as well as other malignancies of the head and neck.

To prepare the therapeutic compositions to be administered according to this invention the hydroxyurea or 1-ethyl-1-hydroxyurea is incorporated in various pharmaceutical preparations by mixing effective amounts thereof with a suitable proportion of a compatible non-toxic pharmaceutical carrier. Illustratively, the formulation may comprise tablets or two-piece gelatin capsules for oral administration, prepared by mixing the compounds with solid carriers, such as starches, gums, talc, sugar and the like; or isotonic liquid preparations for parenteral administration, prepared by suspending the compound in water and adjusting the salinity of the resulting solution. Other dosage-unit forms suitable for oral or parenteral administration can also be employed. Thus, compositions may be prepared using a liquid pharmaceutical carrier such as a carbohydrate containing syrup or an aqueous-alcohol vehicle.

The proportions of active ingredient in the compositions administered according to the present invention may be varied over a substantial range, subject to the practical limitation that sufficient proportion of active ingredient is present to provide a suitable dosage. Obviously, the conventional practice of administering several unit dosage forms at about the same time can be followed. The ingredient should be present in an amount to provide a dosage of from about 5 mg. to about 500 mg. per unit.

The following examples are illustrative, but by no means limitative of such preparations (all temperatures recorded being Centigrade).

EXAMPLE 1

To prepare 1000 tablets, each containing 25 mg. of hydroxyurea, the following ingredients are used:

| Hydroxyurea | 25.0 | g. |
| --- | --- | --- |
| Milk sugar | 164.12 | g. |
| Ethylcellulose | 0.1 | g. |
| Corn starch | 13.0 | g. |
| Talc | 4.7 | g. |
| Magnesium stearate | 1.5 | g. |
| Acacia powder | 2.5 | g. |
| Sodium benzoate | 0.02 | g. |

A tablet granulation is prepared from these ingredients by admixing the hydroxyurea with a starch paste comprising the corn starch, milk sugar, sodium benzoate, ethyl cellulose and acacia powder in a sufficient amount of water to provide a pasty consistency. The mixture is worked until it granulates and then passed through a large mesh (e.g. No. 16) screen. The granules are tray dried at 130° F. for about 5 hours; and the dry granulation is put through a No. 20 (to 24) screen and mixed with the previously sieved talc and magnesium stearate. The resulting granulation is then compressed into tablets, each containing the specified amount of hydroxyurea.

EXAMPLE 2

An elixir of hydroxyurea is prepared by combining the following ingredients:

| | | |
|---|---|---|
| Hydroxyurea | 1.0 | g. |
| Alcohol | 35.0 | cc. |
| Polyethylene Glycol | 35.0 | cc. |
| Sodium cyclohexyl sulfamate | 1.25 | g. |
| Sodium saccharin | 1.25 | g. |
| Water q.s. | 100 | cc. |

In preparing the above composition, the alcohol and polyethylene glycol are mixed together, and the hydroxyurea is then added. The mixture is well stirred and the sodium cyclohexyl sulfamate and sodium saccharin are then added with continued stirring. Sufficient water is then added to bring the volume to 100 cc. Optional ingredients, such as flavoring, may then be added. The resulting elixir is then suitable for administration in the conventional manner, as, for example, by teaspoon in about 5 cc. dosages.

Hydroxyurea may also be provided in a form suitable for oral administration by preparing an aqueous solution thereof; as, for example, by dissolving sufficient hydroxyurea in a predetermined volume of water to provide a 3% solution. Obviously, solutions of varying concentrations of hydroxyurea can be similarly prepared.

EXAMPLE 3

The following ingredients are used for the preparation of 100 dry-fill capsules, each containing 50 mg. of hydroxyurea:

| | | |
|---|---|---|
| Hydroxyurea | 5.0 | g. |
| Lactose | 97.0 | g. |
| Magnesium stearate | 0.8 | g. |

These ingredients are uniformly intermixed in the conventional manner and filled into two-piece hard gelatin capsules to provide capsules each containing 50 mg. of hydroxyurea.

EXAMPLE 4

An aqueous sterile suspension of hydroxyurea providing an effective dose of 50 mg. of hydroxyurea per ml. is prepared by combining the following ingredients:

| | | |
|---|---|---|
| Hydroxyurea | 50.5 | g. |
| Benzyl alcohol | 9.0 | g. |
| Sodium chloride | 6.6 | g. |
| Carboxymethylcellulose | 5.5 | g. |
| Methylcellulose | 0.75 | g. |
| Water q.s. | 1.0 | liter |

The sodium chloride, carboxymethylcellulose and methylcellulose are added to 100 cc. of water with attendant stirring. The hydroxyurea and benzyl alcohol are then added with agitation. Sufficient water is then added to bring the volume to one liter. The resultant suspension is then metered into vials of the selected size as, for example, 10 cc. vials, from which it can be withdrawn for therapeutic application as by intramuscular administration.

EXAMPLE 5

20.0 g. of hydroxyurea are added to a solution of 528 g. of citric acid (anhydrous) in 160 ml. of water and the mixture is stirred until complete solution is obtained. The solution is aseptically filtered, frozen at −30°C. and lyophilized at 50–100 microns vacuum. The resulting solid mixture is filled into sealed vials each containing 2.0 g. of hydroxyurea.

EXAMPLE 6

The following materials are dry blended, then micropulverized:

| | | |
|---|---|---|
| Hydroxyurea | 13,000 | g. |
| Disodium phosphate (anh.) | 936 | g. |
| Citric acid (anh.) | 332.8 | g. |
| Lactose | 7649.2 | g. |
| Magnesium stearate | 182 | g. |

The blended, micropulverized materials are then filled into two-piece gelatin capsules to provide 52,000 capsules each containing 250 mg. of hydroxyurea.

EXAMPLE 7

The following materials are dry blended, then micropulverized:

| | | |
|---|---|---|
| Hydroxyurea | 10,000 | g. |
| Disodium phosphate (anh.) | 720 | g. |
| Citric acid (anh.) | 256 | g. |
| Lactose | 2884 | g. |
| Magnesium stearate | 140 | g. |

The micropulverized blend is then dry filled into two-piece gelatin capsules. 20,000 capsules each containing 500 mg. of hydroxyurea are obtained.

EXAMPLE 8

The following ingredients are used for the preparation of 100 dry-fill capsules each containing 250 mg. of 1-ethyl-1-hydroxyurea:

| | | |
|---|---|---|
| 1-ethyl-1-hydroxyurea | 25.0 | g. |
| Lactose | 31.0 | g. |
| Magnesium stearate | 6.0 | g. |

The three materials are blended and filled into two-piece gelatin capsules each containing 250 mg. of the active ingredient.

Other dosage forms of 1-ethyl-1-hydroxyurea may be produced by substituting this compound for the hydroxyurea in the preceding examples.

What is claimed is:

1. A method of treating malignant neoplastic disease which comprises administering to a host afflicted with such disease a composition comprising about 50 mg. to about 4 gm. of hydroxyurea in pharmaceutical dosage form.

2. A method for the alleviation of malignant neoplastic disease which comprises administering to a human host afflicted with such disease about 20 to 80 mg./kg. per day of hydroxyurea in pharmaceutical dosage form.

3. A method for producing remissions in patients suffering from leukemia, carcinoma or sarcoma which comprises administering to said patient about 50 mg. to 4 gm. of hydroxyurea in one day in a pharmaceutical unit dosage form.

4. A method as in claim 3 for producing remissions in leukemia.

5. A method as in claim 3 for producing remissions in chronic myelocytic leukemia.

6. A method as in claim 4 wherein the amount is 20 to 60 mg./kg. per day.

7. A method as in claim 3 for producing remissions in carcinoma.

8. A method as in claim 7 for producing remissions in carcinoma of the bladder.

9. A method as in claim 7 for producing remissions in carcinoma of the ovary.

10. A method as in claim 3 for producing remissions in melanoma.

* * * * *